(12) United States Patent
Chapuis

(10) Patent No.: US 7,618,934 B2
(45) Date of Patent: Nov. 17, 2009

(54) PERFUMING INGREDIENTS WITH ODOR OF THE PHEROMONE TYPE

(75) Inventor: Christian Chapuis, Mies (CH)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 12/096,888

(22) PCT Filed: Jan. 18, 2007

(86) PCT No.: PCT/IB2007/050161

§ 371 (c)(1),
(2), (4) Date: Jun. 10, 2008

(87) PCT Pub. No.: WO2007/085984

PCT Pub. Date: Aug. 2, 2007

(65) Prior Publication Data

US 2008/0280809 A1    Nov. 13, 2008

(30) Foreign Application Priority Data

Jan. 25, 2006    (WO) ................. PCT/IB2006/050265

(51) Int. Cl.
*A61K 8/18*    (2006.01)
*C07C 45/00*    (2006.01)
*C07C 49/00*    (2006.01)

(52) U.S. Cl. ............................ 512/17; 568/350; 568/374

(58) Field of Classification Search ................... 512/17; 568/350, 374
See application file for complete search history.

(56) References Cited

U.S. PATENT DOCUMENTS

| 3,819,711 | A | * | 6/1974 | Bozzato et al. | ............. 568/350 |
| 4,387,048 | A | | 6/1983 | Yoshida | ...................... 252/522 |
| 5,114,915 | A | | 5/1992 | Fehr et al. | ..................... 512/15 |

\* cited by examiner

*Primary Examiner*—James Seidleck
*Assistant Examiner*—Aaron Greso
(74) *Attorney, Agent, or Firm*—Winston & Strawn LLP

(57) ABSTRACT

The present invention relates to certain β-decalone derivatives which can impart useful odor notes of the pheromone or costus type. The present invention concerns the use of the compounds in the perfumery industry to impart such odor notes as well as to the compositions or articles that contain these compounds.

7 Claims, No Drawings

PERFUMING INGREDIENTS WITH ODOR OF THE PHEROMONE TYPE

This application is a 371 filing of International Patent Application PCT/IB2007/050161 filed Jan. 18, 2007.

TECHNICAL FIELD

The present invention relates to the field of perfumery. More particularly, it concerns some β-decalone derivatives which can impart useful odor notes of the pheromone/costus type. The present invention concerns the use of said compounds in the perfumery industry as well as the compositions or articles containing said compounds.

PRIOR ART

To the best of our knowledge, none of the invention's compounds is known from the prior art.

DESCRIPTION OF THE INVENTION

We have now surprisingly discovered that a compound of formula

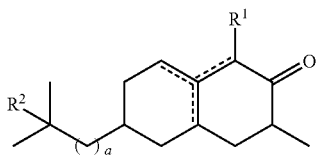

(I)

in the form of any one of its isomers or of a mixture thereof, and wherein the dotted lines indicate the presence of an optionally double bond, $R^1$ represents a methyl group or a hydrogen atom, a represents 0 or 1 and $R^2$ represents a hydrogen atom or a $C_1$-$C_3$ alkyl group;

can be used as perfuming ingredient, for instance to impart odor notes of the pheromone and/or costus type.

According to a particular embodiment of the invention, the compound which has a decaline ring with a trans configuration (i.e. the two hydrogen atoms at the positions 4a and 8a are in a relative trans configuration) is of particular interest, e.g. the compound of formula (II)

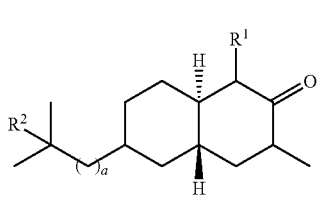

(II)

in the form of any one of its isomers or of a mixture thereof, wherein $R^1$ represents a hydrogen atom or a methyl group, a represent 0 or 1 and $R^2$ represents a hydrogen atom or $C_1$-$C_3$ alkyl group.

According to a particular embodiment of the invention, $R^2$ may represent a methyl or ethyl group.

Yet according to a particular embodiment, the compound of formula

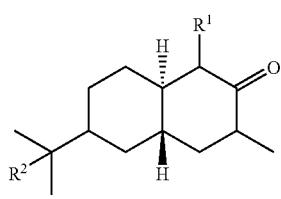

(III)

in the form of any one of its isomers or of a mixture thereof, and wherein the two hydrogen atoms are in a relative configuration trans, $R^1$ represents a hydrogen atom or a methyl group and $R^2$ represents a hydrogen atom or a methyl group;

is also of particular interest.

In particular one may cite also the compound of formula

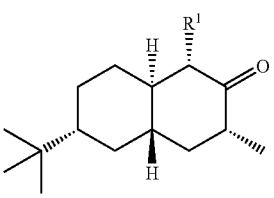

(IV)

in the form of any one of its isomers or of a mixture thereof, and wherein dashed and bold bonds indicate the relative configuration of the hydrogen atoms and of the methyl, tert-butyl and $R^1$ groups, and $R^1$ represents a hydrogen atom or a methyl group, in particular a hydrogen group.

In particular one may cite the compounds 6α-tert-butyl-perhydro-3α-methyl-4aβH,8aαH-2-naphthalenone, 6α-tert-butyl-perhydro-1α,3α-dimethyl-4aβH,8aαH-2-naphthalenone as well as 6α-isopropyl-perhydro-1α,3β-dimethyl-4aβH,8aαH-2-naphthalenone or 6β-(2,2-dimethylpropyl)-perhydro-3α-methyl-4aαH,8aβH-2-naphthalenone.

As mentioned above, the invention's compounds possess odors of particular interest for the perfumery art. In particular said compounds can impart pheromone and/or costus note with a warm aspect.

For example, 6α-tert-butyl-perhydro-1α,3α-dimethyl-4aβH,8aαH-2-naphthalenone can impart a powerful pheromone note characterized by a strong costus connotation, which makes this compound an interesting candidate as replacement of natural Costus.

Another example of the invention is 6α-tert-butyl-perhydro-3α-methyl-4aβH,8aαH-2-naphthalenone, able to impart an unusual pheromone note with an animal aspect completely devoid of any fecal note. The overall note can be described as an unusual warm, pheromone note, with a costus undemote, globally reminding very strongly the α-androstenone. The overall odor of this ingredient is also quite different from, and better than, the odor of natural ingredients like Civet and Castoreum.

A further example of decalone of formula (I) is 6β-(2,2-dimethylpropyl)-perhydro-3α-methyl-4aαH,8aβH-2-naphthalenone, which possesses a very powerful pheromone and costus odor.

Moreover, as derivative of formula (I), one may cite also 6α-isopropyl-perhydro-1α,3β-dimethyl-4aβH,8aαH-2-naphthalenone, which possesses an odor very similar to that of 6α-tert-butyl-perhydro-3α-methyl-4aβH,8aαH-2-naphthalenone but somehow weaker and having also a slight woody note.

Amongst the alkenes of formula (I), one may cite a mixture of 6-tert-butyl-3-methyl-3,4,4A,5,6,7-hexahydro-2(1H)-naphthalenone and 6-tert-butyl-3-methyl-3,4,5,6,7,8-hexahydro-2(1H)-naphthalenone, which possesses a pheromone odor with light curry note.

It is also important to point out that the invention's compounds is a "perfuming compound" because of the particular combination of odor tonalities and character as well as of intensity or power and persistence of its scent. Indeed such particular combination allows imparting a hedonic effect. In other words the invention's compound is able to impart or modify in a positive or pleasant way the odor of a composition in which they are added, and not just as "imparting an odor".

As mentioned above, the invention concerns the use of a compound of formula (I) as perfuming ingredient. In other words it concerns a method to confer, enhance, improve or modify the odor properties of a perfuming composition or of a perfumed article, which method comprises adding to said composition or article an effective amount of at least a compound of formula (I). In particular said method can be applied to impart pheromone and/or costus type notes.

By "use of a compound of formula (I)" it has to be understood here also the use of any composition containing compound (I) and which can be advantageously employed in perfumery industry as active ingredients.

Said compositions, which in fact can be advantageously employed as perfuming ingredient, are also an object of the present invention.

Therefore, another object of the present invention is a perfuming composition comprising:
 i) as perfuming ingredient, at least one invention's compound as defined above;
 ii) at least one ingredient selected from the group consisting of a perfumery carrier and a perfumery base; and
 iii) optionally at least one perfumery adjuvant.

By "perfumery carrier" we mean here a material which is practically neutral from a perfumery point of view, i.e. that does not significantly alter the organoleptic properties of perfuming ingredients. Said carrier may be a liquid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting example solvents such as dipropyleneglycol, diethyl phthalate, isopropyl myristate, benzyl benzoate, 2-(2-ethoxyethoxy)-1-ethanol or ethyl citrate, which are the most commonly used.

By "perfumery base" we mean here a composition comprising at least one perfuming co-ingredient.

Said perfuming co-ingredient is not of the formula (I). Moreover, by "perfuming co-ingredient" it is meant here a compound, which is used in perfuming preparation or composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of its general knowledge and according to intended use or application and the desired organoleptic effect. In general terms, these perfuming co-ingredients belong to chemical classes as varied as alcohols, aldehydes, ketones, esters, ethers, acetates, nitriles, terpene hydrocarbons, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

For the compositions which comprise both a perfumery carrier and a perfumery base, other suitable perfumery carrier, than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company).

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

An invention's composition consisting of at least one compound of formula (I) and at least one perfumery carrier represents a particular embodiment of the invention as well as a perfuming composition comprising at least one compound of formula (I), at least one perfumery carrier, at least one perfumery base, and optionally at least one perfumery adjuvant.

It is useful to mention here that the possibility to have, in the compositions mentioned above, more than one compound of formula (I) is important as it enables the perfumer to prepare accords, perfumes, possessing the odor tonality of various compounds of the invention, creating thus new tools for their work.

Preferably, any mixture resulting directly from a chemical synthesis, e.g. without an adequate purification, in which the compound of the invention would be involved as a starting, intermediate or end-product could not be considered as a perfuming composition according to the invention.

Furthermore, the invention's compound can also be advantageously used in all the fields of modern perfumery to positively impart or modify the odor of a consumer product into which said compound (I) is added. Consequently, a perfumed article comprising:
 i) as perfuming ingredient, at least one compound of formula (I), as defined above, or an invention's perfuming composition; and
 ii) a consumer product base;

is also an object of the present invention.

For the sake of clarity, it has to be mentioned that, by "consumer product base" we mean here a consumer product, which is compatible with perfuming ingredients. In other words, a perfumed article according to the invention comprises the functional formulation, as well as optionally additional benefit agents, corresponding to a consumer product, e.g. a detergent or an air freshener, and an olfactive effective amount of at least one invention's compound.

The nature and type of the constituents of the consumer product do not warrant a more detailed description here, which in any case would not be exhaustive, the skilled person being able to select them on the basis of its general knowledge and according to the nature and the desired effect of said product.

Examples of suitable consumer product bases include solid or liquid detergents and fabric softeners as well as all the other articles common in perfumery, namely perfumes, colognes or after-shave lotions, perfumed soaps, shower or bath salts, mousses, oils or gels, hygiene products or hair care products such as shampoos, body-care products, deodorants or antiperspirants, air fresheners and also cosmetic preparations. As detergents there are intended applications such as detergent compositions or cleaning products for washing up or for cleaning various surfaces, e.g. intended for textile, dish or hard-surface treatment, whether they are intended for domestic or industrial use. Other perfumed articles are fabric refreshers, ironing waters, papers, wipes or bleaches.

Some of the above-mentioned consumer product bases may represent an aggressive medium for the invention's compound, so that it may be necessary to protect the latter from premature decomposition, for example by encapsulation.

The proportions in which the compounds according to the invention can be incorporated into the various aforementioned articles or compositions vary within a wide range of values. These values are dependent on the nature of the article to be perfumed and on the desired organoleptic effect as well as the nature of the co-ingredients in a given base when the compounds according to the invention are mixed with perfuming co-ingredients, solvents or additives commonly used in the art.

For example, in the case of perfuming compositions, typical concentrations are in the order of 0.01% to 3% by weight, or even more, of the compounds of the invention based on the weight of the composition into which they are incorporated. Concentrations lower than these, such as in the order of 0.001% to 1% by weight, can be used when these compounds are incorporated into perfumed articles, percentage being relative to the weight of the article.

The preparation of the invention's compound is illustrated further below in the examples. The methods described can be used also for the preparation of the analogous compound not explicitly described in the example and having a structure according to formula (I).

EXAMPLES

The invention will now be described in further detail by way of the following examples, wherein the abbreviations have the usual meaning in the art, the temperatures are indicated in degrees centigrade (° C.); the NMR spectral data were recorded in $CDCl_3$ (if not stated otherwise) with a 360 or 400 MHz machine for $^1H$ and $^{13}C$, the chemical displacements δ are indicated in ppm with respect to TMS as standard, the coupling constants J are expressed in Hz.

Example 1

Synthesis of Compounds of Formula (I)

Procedure A $NH_3$ (290 ml) was condensed at −60°, and Li (1.12 g, 160 mol) was added. Then a solution of the enone (1) or (2) (40 mmol) in $Et_2O$ (12 ml) and tBuOH (4.5 ml) was added dropwise. After 8 hour at −33°, and 18 h for evaporation of $NH_3$, the reaction mixture was diluted with $Et_2O$ (90 ml), poured onto ice and the mixture was washed with saturated aqueous $NH_4Cl$, $H_2O$ to neutral, dried ($Na_2SO_4$), concentrated, and the residue was purified by chromatography and/or distillation to afford the desired ketone.

Procedure B nBuLi (21.3 ml, 2.5M in hexane, 53 mmol) was added dropwise to a solution of diisopropyl amine (5.4 g, 53 mmol) in THF (70 ml) at −20°. After 0.5 h a solution of enone (4) (48 mmol) in THF (30 ml) was added dropwise followed after 0.5 h by MeI (3.3 ml, 7.6 g, 53 mmol). After 4 h at 20° the reaction mixture was poured onto ice, acidified with 10% aqueous HCl (40 ml), then extracted with $Et_2O$. The org. phase was washed to neutral with $H_2O$, dried ($Na_2SO_4$), concentrated and purified by CC and/or distillation to afford the desired ketone.

A) Preparation of 6α-tert-butyl-perhydro-1α,3α-dimethyl-4aβH,8aαH-2-naphthalenone 6α-Tert-Butyl-1,3α-Dimethyl-4-4aβ5,6,7,8-hexahydro-2(3H)-naphthalenone (1)

Obtained in 74% yield from 6α-tert-Butyl-4,4aβ5,6,7,8-hexahydro-1-methyl-2(3H)-naphthalenone (4) according to the procedure B after distillation. Bp: 112°/0.3 mbar.

$^1$H-NMR: 0.89 (s, 3H); 1.10 (d, J=7, 3H); 1.11 (m, 1H); 1.18 (q, J=14, 1H); 1.38 (tt, J=5; 14, 1H); 1.72 (m, 1H); 1.78 (brs, 3H); 1.88 (m, 2H); 1.97 (m, 2H); 2.32 (m, 1H); 2.46 (m, 1H); 2.87 (m, 1H).

$^{13}$C-NMR: 10.8 (q), 16.0 (q), 27.6 (3q), 28.2 (t), 31.8 (t), 32.4 (s), 35.6 (t), 36.0 (t), 36.6 (d), 38.2 (d), 47.7 (d), 126.4 (s), 158.7 (s), 202.6 (s).

Perhydro-6α-tert-butyl-1α,3α-dimethyl-4aβH, 8aαH-2-naphthalenone

Obtained in 11% yield from (1) according to the procedure A after chromatography ($SiO_2$, cyclohexane/AcOEt 98:2). Bp: 120°/0.7 mbar.

$^1$H-NMR: 0.71 (q, J=14, 1H); 0.86 (s, 9H); 0.9 (m, 2H); 0.99 (d, J=7, 3H); 1.01 (d, J=7, 3H); 1.05 (m, 1H); 1.13 (m, 2H); 1.52 (m, 1H); 1.74-1.84 (m, 2H); 1.99 (m, 2H); 2.1 (m, 1H); 2.47 (m, 1H).

$^{13}$C-NMR: 11.3 (q), 14.6 (q), 26.6 (t), 27.5 (3q), 32.0 (t), 32.3 (s), 33.9 (t), 42.2 (d), 43.8 (t), 44.7 (d), 47.6 (d), 49.7 (d), 50.6 (d), 214.4 (s).

B) Preparation of 6α-tert-butyl-perhydro-3α-methyl-4aβH,8aαH-2-naphthalenone

6-α-tert-Butyl-3α-methyl-4,4aβ,5,6,7,8-hexahydro-2(3H)-naphthalenone (2)

A mixture of 4-tert-butyl-cyclohexanone (1.0 mol), morpholine (131 g, 1.5 mol), and pTsOH (1.1 g, 6.4 mmol) in cyclohexane (2000 ml), was heated under reflux for 12 hours, and $H_2O$ formed was collected with a Dean-Stark apparatus. $Na_2CO_3$ (1.1 g, 10.4 mmol) was added to the cold solution. The solution was filtered, dried, and concentrated, and the crude oil was distilled under vacuum to afford the corresponding enamine.

A solution of the enamine (0.92 mol), and 3-methylbutenone (95 g, 1.13 mol) in toluene (1500 ml), was heated under reflux for 30 hours. A 50% aqueous AcOH solution (70 ml) was added to the cold mixture, and heated at reflux for 1 h, then cooled. The cold mixture was extracted. The organic phase was washed with 15% aqueous HCl solution, $H_2O$, and brine to neutral, dried ($Na_2SO_4$), and concentrated under vacuum. The crude intermediate thus obtained and pTsOH (0.21 g, 1.22 mmol) in toluene (2100 ml) was heated under reflux for 18 h, and $H_2O$ formed was separated with a Dean-Stark apparatus. The cold solution was washed with saturated aqueous $NaHCO_3$ solution, $H_2O$, and brine, dried, and concentrated in vacuo. The crude oil was purified by chromatography ($SiO_2$, cyclohexane/AcOEt 97:3) to afford the desired product, obtained in 28% yield. Bp 117°/0.3 mbar.

$^1$H-NMR: 0.88 (s, 9H); 1.11 (d, 3H); 1.18 (dt, J=5, 10, 1H); 1.29 (m, 1H); 1.39 (m, 1H); 1.92 (m, 2H); 1.98 (m, 1H); 2.05 (dt, J=5, 12, 1H); 2.22 (dt, J=5, 12, 1H); 2.33 (m, 1H); 2.39 (m, 1H); 2.50 (m, 1H); 5.79 (s, 1H).

$^{13}$C-NMR: 14.7 (q), 27.5 (t), 27.5 (3q), 32.4 (s), 35.1 (t), 35.8 (t), 38.5 (d), 38.6 (t), 40.6 (d), 47.0 (d), 123.8 (d), 165.8 (s), 202.2 (s).

Perhydro-6α-tertbutyl-3α-methyl-4aβH,8aαH-2-naphtalenone

Obtained in 45% yield, from (2), as a 1:1 mixture according to the procedure A after chromatography (SiO$_2$, CH$_2$Cl$_2$). Bp: 110°/0.64 mbar.

$^1$H-NMR: 0.73 (m, 1H); 0.86 (s, 9H); 1.01 (d, J=7, 3H); 1.11 (m, 2H); 1.27 (m, 1H); 1.60 (dt, J=7, 14, 1H); 1.69 (m, 1H); 1.76 (m, 2H); 1.80 (m, 1H); 1.97 (m, 1H); 2.07 (m, 1H); 2.19 (m, 1H); 2.33 (m, 1H); 2.42 (m, 1H).

$^{13}$C-NMR: 14.4 (q), 27.6 (3q), 26.5 (t), 32.4 (s), 33.5 (t), 34.3 (t), 42.4 (d), 43.2 (t), 44.3 (d), 44.8 (d), 47.9 (d), 48.4 (t), 212.8 (s).

Example 2

Synthesis of Compounds of Formula (I)

1) 6α-(2,2-Dimethylpropyl)-3-methyl-4aβH8aαH-perhydro-2-naphtalenone

6α-(2,2-dimethylpropyl)-3-methyl-4,4aβ,5,6,7,8-hexahydro-2(3H)-naphthalenone nBuLi (2.5 ml, 1.6M, 4 mmol) was added at −40° C. to a solution of diisopropylamine (0.4 g, 4 mmol) in THF (7 ml). After 0.5 hour, a solution of known 6α-(2,2-dimethylpropyl)-4,4aβ,5,6,7,8-hexahydro-2(3H)-naphthalenone (0.8 g, 3.6 mmol, C. Chapuis, *Chem. & Biodiv.* 2004, 1, 980) in THF (3 ml) was added dropwise. After 0.5 hour, iodomethane (0.7 g, 0.3 ml, 4 mmol) was added dropwise and the temperature was slowly equilibrated to 20° C. After 4 hours at 20° C. the reaction mixture was poured onto ice (20 ml), acidified with 10% HCl, extracted with Et$_2$O. The organic phase was washed to neutrality with H$_2$O, dried (MgSO$_4$), filtered, concentrated and purified by CC on SiO$_2$ (cyclohexane/AcOEt 95:5) to afford the desired enone as a 15:85 mixture of isomers in 28% yield (Bp 118°/0.2 mbar).

IR: 2951, 2930, 2867, 1670, 1625, 1455, 1363, 1325, 1250, 1211, 872.

$^1$H-NMR: 0.92 (s, 9H), 1.11 (d, J=7, 3H); 1.1-1.4 (m, 2H); 1.65 (m, 2H); 1.75 (m, 2H); 1.85 (m, 2H); 1.95 (m, 2H); 2.25 (m, 1H); 2.4 (m, 2H); 5.74 (brs, 1H).

$^{13}$C-NMR: 15.9 (q), 30.0 (3q), 31.0 (s), 33.9 (d), 35.5 (d), 35.7 (t), 36.0 (t), 36.4 (t), 38.7 (d), 43.2 (t), 50.5 (t), 122.3 (d), 166.1 (s), 203.2 (s).

6α-(2,2-Dimethylpropyl)-3-methyl-4aβH8aαH-perhydro-2-naphtalenone

The compound was obtained using Procedure A provided in Example 1. Starting from 6α-(2,2-dimethylpropyl)-3-methyl-4,4aβ,5,6,7,8-hexahydro-2(3H)-naphthalenone (240 mg, 1 mmol) and after purification by CC with cyclohexane/AcOEt 95:5 the title compound was obtained in 23% yield Bp: 115°/0.3.

IR: 2950, 2909, 2865, 2847, 1711, 1455, 1363, 1248, 1213, 1178, 1010, 939.

$^1$H-NMR: 0.90 (s, 3H); 1.20 (d, J=7, 3H); 0.7-1.3 (m, 3H); 1.4-1.8 (m, 8H); 1.9-2.6 (m, 5H).

2) 6-α-tert-Butyl-3-methyl-4,4aβ,5,6,7,8-hexahydro-2(3H)-naphthalenone

Cis-4-tert-butyl-2-(2-methyl-3-oxobutyl)-1-cyclohexanone

A solution of the pure 4-(4-tert-butyl-1-cyclohexen-1-yl) morpholine (0.92 mol), and 3-methylbutenone (95 g, 1.13 mol) in toluene (1500 ml), was heated under reflux for 30 hours. A 50% aqueous AcOH solution (70 ml) was added to the cold mixture, and heated at reflux for 1 hour, then cooled. The cold mixture was extracted. The organic phase was washed with 15% aqueous HCl solution, H$_2$O, and brine to neutral, dried (Na$_2$SO$_4$), and concentrated under vacuum. The diketone was thus obtained quantitatively as a crude intermediate.

IR: 2963, 1716, 1459, 1366, 1227, 1177.

$^1$H-NMR: 0.89 (s, 9H); 0.90 (d, J=7, 3H); 1.09 (m, 3H); 1.3-2.0 (m, 5H); 2.13 (s, 3H); 2.33 (m, 2H); 2.51 (m, 1H).

$^{13}$C-NMR: 17.4 (q), 27.7 (3q), 28.4 (q), 28.9 (t), 32.4 (s), 32.8 (t), 36.2 (t), 41.8 (t), 45.1 (d), 47.1 (d), 47.6 (d), 213.0 (s), 213.4 (s).

6-α-tert-Butyl-3-methyl-4,4aβ,5,6,7,8-hexahydro-2(3H)-naphthalenone

A solution of cis-4-tert-butyl-2-(2-methyl-3-oxobutyl)-1-cyclohexanone (0.83 mol) and pTsOH (0.21 g, 1.22 mmol) in toluene (2100 ml) was heated under reflux for 18 h, and H$_2$O formed was separated with a Dean-Stark apparatus. The cold solution was washed with saturated aqueous NaHCO$_3$ solution, H$_2$O, and brine, dried, and concentrated in vacuo. Obtained in 28% yield CC (SiO$_2$, cyclohexane/AcOEt 97:3). Bp 117°/0.3 mbar.

Stereoisomer with 3βMe pseudo-axial:
IR: 2943, 2865, 1672, 1627, 1451, 1365, 1210, 876.
$^1$H-NMR: 0.89 (m, 9H); 1.1-1.2 (m, 2H); 1.12 (d, J=7, 3H); 1.35 (tt, J=2, 9, 1H); 1.78 (m, 1H); 1.9-2.0 (m, 3H); 2.22 (dt, J=4, 9, 1H); 2.36 (m, 1H); 2.44 (m, 2H); 5.74 (brs, 1H).
$^{13}$C-NMR: 15.9 (q), 27.6 (3q), 28.5 (t), 32.5 (s), 35.4 (t), 35.6 (d), 35.7 (t), 36.2 (t), 38.8 (d), 47.6 (d), 122.1 (d), 166.5 (s), 203.2 (s).

Stereoisomer with 3αMe pseudo-equatorial:
IR: 2939, 2866, 1670, 1626, 1455, 1364, 1209, 875.
$^1$H-NMR: 0.88 (s, 9H); 1.11 (d, J=7, 3H); 1.17 (dt, J=5, 14, 1H); 1.29 (tt, J=2, 12, 1H); 1.28 (m, 2H); 1.92 (m, 1H); 1.97 (m, 1H); 2.05 (dt, J=5, 14, 1H); 2.22 (m, 1H); 2.32 (m, 1H); 2.36 (m, 1H); 2.49 (dt, J=3, 14, 1H); 5.79 (brs, 1H).
$^{13}$C-NMR: 14.7 (q), 27.5 (t), 27.5 (3q), 32.4 (s), 35.1 (t), 35.8 (t), 38.5 (d), 38.6 (t), 40.6 (d), 47.0 (d), 123.8 (d), 165.8 (s), 202.2 (s). MS: 220 (48, M$^+$), 205 (6), 178 (100), 163 (21), 149 (12), 135 (10), 122 (38), 94 (57), 91 (21), 57 (34).

3) Mixture of 6α-tert-Butyl-3-methyl-3,4,4 μl, 5,6,7-hexahydro-2(1H)-naphthalen one and 6-tert-Butyl-3-methyl-3,4,5,6,7,8-hexahydro-2(1H)-naphthalenone 6-α-tert-Butyl-3-methyl-4,4aβ,5,6,7,8-hexahydro-2(3H)-naphthalenone (1.85 g, 8.4 mmol) in DMF (2 ml) was added dropwise to a suspension of tBuOK (1.4 g, 12.5 mmol) in DMF (6 ml) at 15° C. After 18 h at 20° C., 50% AcOH (8 ml) was added and the reaction mixture was extracted with Et$_2$O. The organic phase was washed with brine to neutrality, dried (Na$_2$SO$_4$), filtered, concentrated and purified by CC on SiO$_2$ with cyclohexane/AcOEt 98:2 to afford a 56:44 mixture of 6α-tert-butyl-3-methyl-3,4,4aβ,5,6,7-hexahydro-2(1H)-naphthalenone and of 6-tert-butyl-3-methyl-3,4,5,6,7,8-hexahydro-2(1H)-naphthalenone in 30% yield.

Bp: 95° C./0.3 mbar.

6α-tert-Butyl-3-methyl-3,4,4Aβ,5,6,7-hexahydro-2(1H)-naphthalenone IR: 2961, 2868, 1716, 1469, 1455, 1364, 1240, 1214, 1165, 1083, 908.

$^1$H-NMR: 0.88 (s, 9H), 1.03 (d, J=7, 3H); 1.0-1.4 (m, 2H); 1.5-2.1 (m, 4H); 2.3-2.5 (m, 2H); 2.65 (m, 1H); 2.8-3.2 (m, 2H); 5.42 (m, 1H).

6-tert-Butyl-3-methyl-3,4,5,6,7,8-hexahydro-2(1H)-naphthalenone

IR: 2925, 2869, 1717, 1675, 1456, 1394, 1364, 1213, 1157, 1062, 878.

$^1$H-NMR: 0.88 (s, 9H); 1.08 (d, J=7, 3H); 0.8-1.4 (m, 3H); 1.7-2.1 (m, 6H); 2.1-2.7 (m, 3H).

4) Perhydro-6α-isopropyl-1α,3β-dimethyl-4aβH, 8aαH-2-naphthalenone

6α-Isopropyl-1,3α-Dimethyl-4-4aβ,5,6,7,8-hexahydro-2(3H)-naphthalenone nBuLi (21.3 ml, 2.5M in hexane, 53 mmol) was added dropwise to a solution of diisopropyl amine (5.4 g, 53 mmol) in THF (70 ml) at −20°. After 0.5 hour a solution of 4,4aβ,5,6,7,8-hexahydro-6α-isopropyl-1-methyl-2(3H)-naphthalenone (48 mmol) (C. Chapuis, *Chem. & Biodiv.* 2004, 1, 980) in THF (30 ml) was added dropwise followed after 0.5 hours by MeI (3.3 ml, 7.6 g, 53 mmol). After 4 hours at 20° the reaction mixture was poured onto ice, acidified with 10% HCl (40 ml), then extracted with Et$_2$O. The organic phase was washed to neutral with H$_2$O, dried (Na$_2$SO$_4$), concentrated and purified by distillation to yield the desired compound in 73% yield.

Bp: 102°/0.3 mbar.

IR: 2930, 2870, 1665, 1451, 1377, 1322, 1240, 1026.

$^1$H-NMR: 0.90 (d, J=7, 6H); 1.10 (d, J=7, 3H); 1.11 (m, 1H); 1.18 (q, J=14, 1H); 1.4 (m, 1H); 1.47 (hept, J=7, 1H); 1.73 (dt, J=7, 10, 1H); 1.78 (brs, 3H); 1.86 (m, 2H); 1.94 (m, 2H); 2.33 (m, 1H); 2.46 (m, 1H); 2.85 (m, 1H).

$^{13}$C-NMR: 10.9 (q), 16.0 (q), 19.9 (q), 20.0 (q), 30.5 (t), 31.7 (t), 32.4 (d), 36.0 (t), 36.6 (d), 37.7 (d), 38.1 (d), 43.7 (d), 126.6 (s), 158.8 (s), 202.7 (s).

Perhydro-6α-isopropyl-1α,3β-dimethyl-4aβH,8aαH-2-naphthalenone

The compound was obtained using Procedure A provided in Example 1. Starting from 6α-isopropyl-1,3α-dimethyl-4-4aβ,5,6,7,8-hexahydro-2(3H)-naphthalenone and after purification by CC (SiO$_2$, cyclohexane/AcOEt 98:2) the title compound was obtained in 45% yield.

Bp: 120°/0.5 mbar.

IR: 2972, 2944, 2903, 2867, 2847, 1694, 1449, 1380, 967, 929.

$^1$H-NMR: 0.70 (m, 1H); 0.88 (d, J=7, 3H); 0.89 (d, J=7, 3H); 0.91 (m, 2H); 0.99 (d, J=7, 3H); 1.05 (m, 1H); 1.15 (m, 1H); 1.21 (d, J=7, 3H); 1.43 (oct, J=7, 1H); 1.62 (m, 2H); 1.68 (m, 2H); 1.77 (m, 1H); 1.98 (m, 1H); 2.28 (sext, 1H); 2.61 (m, 1H).

$^{13}$C-NMR: 11.4 (q), 18.0 (q), 19.8 (q), 19.9 (q), 29.1 (t), 31.6 (t), 32.7 (d), 36.1 (d), 36.6 (t), 40.4 (t), 43.6 (d), 44.3 (d), 45.6 (d), 49.7 (d), 217.1 (s).

Example 3

Preparation of a Perfuming Composition

An Eau de toilette for woman type was prepared by admixing the following ingredients

| Ingredient | Parts by weight |
|---|---|
| 10%* Isoeugenyl acetate | 20 |
| 10%* Cinnamyl acetate | 30 |
| Styrallyl acetate | 20 |
| Bergamote essential oil | 195 |
| 1%* Ethyl caproate | 10 |
| 10%* Cardamome essential oil | 40 |
| 10%* Carvacrol | 30 |
| 10%* Cetalox ® Laevo[1) | 80 |
| 4-Cyclohexyl-2-methyl-2-butanol | 230 |
| 10%* Alpha damascone | 10 |
| Decal | 5 |
| 10%* Delta damascone | 10 |
| 10%* Ethylvanilline | 80 |
| Exaltolide ®[2) | 180 |
| 10%* Geranium essential oil | 40 |
| Habanolide ®[3) | 700 |
| Hedione ®[4) | 800 |
| 3-(1,3-Benzodioxol-5-yl)-2-methylpropanal | 10 |
| Helvetolide ®[5) | 50 |
| Hivernal ®[6) | 10 |
| Iralia ®[7) | 20 |
| Iso E Super ®[8) | 40 |
| Muscenone Delta ®[9) | 30 |
| 1,3-Dimethyl-3-phenylbutyl acetate | 15 |
| Patchouli essential oil | 100 |
| Polysantol ®[10) | 120 |
| 2-Benzyl-4,4,6-trimethyl-1,3-dioxane | 10 |
| Romandolide ®[11) | 500 |
| Rose Petales | 5 |
| Cis-3-Hexenyl salicylate | 80 |
| | 3470 |

*in dipropyleneglycol
[1)dodecahydro-3a,6,6,9a-tetramethyl-naphtho[2,1-b]furan; origin: Firmenich SA, Switzerland
[2)pentadecanolide; origin: Firmenich SA, Switzerland
[3)pentadecenolide; origin: Firmenich SA, Switzerland
[4)methyl dihydrojasmonate; origin: Firmenich SA, Switzerland
[5)(1S,1'R)-2-[1-(3',3'-dimethyl-1'-cyclohexyl)ethoxy]-2-methylpropyl propanoate; origin: Firmenich SA, Switzerland
[6)3-(3,3-dimethyl-5-indanyl)propanal and 3-(1,1-dimethyl-5-indanyl)propanal; origin: Firmenich SA, Switzerland
[7)mixture of isomers of methylionones; origin: Firmenich SA, Switzerland
[8)1-(octahydro-2,3,8,8-tetramethyl-2-naphtalenyl)-1-ethanone; origin: IFF, USA
[9)3-methyl-cyclopentadecenone; origin: Firmenich SA, Switzerland
[10)(1'R,E)-3,3-Dimethyl-5-(2',2',3'-trimethyl-3'-cyclopenten-1'-yl)-4-penten-2-ol; origin: Firmenich SA, Switzerland
[11)[1-(3',3'-Dimethyl-1'-cyclohexyl)ethoxycarbonyl]methyl propanoate; origin: Firmenich SA, Switzerland The addition of 30 parts by weight of 6α-tert-butyl-perhydro-3α-methyl-4aβH,8aαH-2-naphthalenone imparted to the above-described eau de toilette an attractive warm pheromone connotation, which exalts the musk-animal aspect of the original eau de toilette.

The addition of 30 parts by weight of 6α-tert-butyl-perhydro-1α,3α-dimethyl-4aβH,8a αH-2-naphthalenone provided a perfume which distinguished from the precedent by having a pheromone-masculin note less developed but a costus note much more stronger and developed.

Example 4

Preparation of a Perfuming Composition

A perfuming composition for woman was prepared by admixing the following ingredients:

| Ingredient | Parts by weight |
|---|---|
| Isoeugenyl acetate | 40 |
| Benzyl acetate | 200 |
| Geranyl acetate | 20 |
| Linalyl acetate | 130 |

-continued

| Ingredient | Parts by weight |
|---|---|
| 10%* Cis-3-Hexenyl acetate | 50 |
| Styrallyl acetate | 25 |
| 1%* C 12 aldehyde | 20 |
| 1%* Dodecenal | 10 |
| 1%* Phenylacetic aldehyde | 40 |
| Allyl amyl glycolate | 10 |
| 10%* Gamma undecalactone | 50 |
| 10%* Gamma nonalactone | 40 |
| 10%* Cetalox ®[1] | 40 |
| Citronellol | 30 |
| Coumarine | 100 |
| 10%* Damascenone | 20 |
| 10%* Alpha damascone | 40 |
| (1'R,E)-2-Ethyl-4-(2',2',3'-trimethyl-3'-cyclopenten-1'-yl)-2-buten-1-ol | 110 |
| Delta Damascone | 10 |
| Ethylvanilline | 40 |
| 50%** Galaxolide ®[2] | 400 |
| Galbex ® 183[3] | 20 |
| Geraniol | 70 |
| Hedione ®[4] | 760 |
| 10%* Indol | 10 |
| Iralia ®[5] | 50 |
| Iso E Super ®[6] | 100 |
| Linalol | 230 |
| Mandarine essential oil | 40 |
| 10%* Methyl octinecarbonate | 10 |
| 10%* Methyl naphthyl ketone | 55 |
| 10%* Cristal moss | 55 |
| Muscenone Delta[7] | 25 |
| 10%* Rose Oxide | 20 |
| Phenethylol | 80 |
| Orange essential oil | 70 |
| Romandolide ®[8] | 200 |
| Benzyl salicylate | 140 |
| Cis-3-Hexenyl salicylate | 60 |
| 3-Methyl-5-(2,2,3-trimethyl-3-cyclopenten-1-yl)-2-pentanol | 100 |
| Terpineol | 60 |
| 10%* Vanilline | 50 |
| Vertofix Coeur IFF | 200 |
| Ylang Extra | 60 |
| | 3890 |

*in dipropyleneglycol
**in MIP
[1] dodecahydro-3a,6,6,9a-tetramethyl-naphtho[2,1-b]furan; origin: Firmenich SA, Switzerland;
[2] 1,3,4,6,7,8-hexahydro-4,6,6,7,8,8-hexamethyl-cyclopenta-g-2-benzopyrane; origin: International Flavors & Fragrances, USA
[3] compounded perfumery base; origin: Firmenich SA, Switzerland;
[4] methyl dihydrojasmonate; origin: Firmenich SA, Switzerland;
[5] mixture of isomers of methylionones; origin: Firmenich SA, Switzerland;
[6] 1-(octahydro-2,3,8,8-tetramethyl-2-naphtalenyl)-1-ethanone; origin: IFF, USA;
[7] 3-methyl-cyclopentadecenone; origin: Firmenich SA, Switzerland;
[8] [1-(3',3'-Dimethyl-1'-cyclohexyl)ethoxycarbonyl]methyl propanoate; origin: Firmenich SA, Switzerland;
[9] Methyl cedryl ketone; origin: International Flavors & Fragrances, USA The addition of 10 parts by weight of 6α-tert-butyl-perhydro-3α-methyl-4aβH,8aαH-2-naphthalenone imparted to the cologne a much warmer and dry pheromone note, wherein the animal aspect of the original perfume is much more striking despite the very small amount of invention's compound added.

The addition of 10 parts by weight of 6α-tert-butyl-perhydro-1α,3α-dimethyl-4aβH,8a αH-2-naphthalenone confers a less developed pheromone note but with a stronger costus note, or much more in the direction of a costus character.

The invention claimed is:

1. A compound selected from the group consisting of 6α-tert-butyl-perhydro-3α-methyl-4aβH,8aαH-2-naphthalenone, 6α-tert-butyl-perhydro -1α,3α-dimethyl-4aβH,8aαH-2-naphthalenone, 6α-isopropyl-perhydro-1α,3β-dimethyl -4aβH,8aαH-2-naphthalenone and 6β-(2,2-dimethylpropyl)-perhydro-3α-methyl-4aαH,8aβH -2-naphthalenone.

2. A method to confer, enhance, improve or modify the odor properties of a perfuming composition or of a perfumed article, which method comprises adding to the composition or article an effective amount of at least a compound of claim 1.

3. The method according to claim 2, wherein the compound is present in an amount to provide pheromone or costus type notes to the perfuming composition or perfumed product.

4. The method according to claim 2, wherein the compound is added to the perfuming composition in an amount of between 0.001% to 3% by weight, based on the total weight of the composition into which they are incorporated.

5. A perfuming composition comprising:
 i) as a perfuming ingredient, at least compound as recited in claim 1;
 ii) at least one ingredient selected from the group consisting of a perfumery carrier and a perfumery base; and
 iii) optionally at least one perfumery adjuvant.

6. A perfumed article comprising:
 i) as a perfuming ingredient, at least compound as recited in claim 1; and
 ii) a consumer product base.

7. A perfumed article according to claim 6, wherein the consumer product base is a solid or liquid detergent, a fabric softener, a perfume, a cologne or after-shave lotion, a perfumed soap, a shower or bath salt, mousse, oil or gel, a hygiene product, a hair care product, a shampoo, a body-care product, a deodorant or antiperspirant, an air freshener, a cosmetic preparation, a fabric refresher, an ironing water, a paper, a wipe or a bleach.

* * * * *